United States Patent
Mohajer

(10) Patent No.: US 9,134,204 B2
(45) Date of Patent: Sep. 15, 2015

(54) APPARATUS AND METHOD FOR MAINTAINING CONSISTENT FLUID VELOCITY AND HOMOGENEITY IN A PIPELINE

(75) Inventor: Kam Mohajer, Edwards, CO (US)

(73) Assignee: KAM Controls, Inc., Houston, TX (US)

( * ) Notice: Subject to any disclaimer, the term of this patent is extended or adjusted under 35 U.S.C. 154(b) by 403 days.

(21) Appl. No.: 13/507,653

(22) Filed: Jul. 17, 2012

(65) Prior Publication Data

US 2013/0036800 A1 Feb. 14, 2013

Related U.S. Application Data

(60) Provisional application No. 61/574,712, filed on Aug. 8, 2011.

(51) Int. Cl.
*G01N 1/00* (2006.01)
*G01N 1/20* (2006.01)

(52) U.S. Cl.
CPC ...... *G01N 1/2035* (2013.01); *G01N 2001/2064* (2013.01); *Y10T 137/85978* (2015.04)

(58) Field of Classification Search
CPC ....................................................... G01N 1/14
USPC .............. 73/19.04, 19.09, 19.1, 61.41–61.61, 73/863.41, 863.43, 863.51, 863.61, 73/863.81, 863.83, 863.85, 864.34, 73/864.73; 137/565.01–565.24
See application file for complete search history.

(56) References Cited

U.S. PATENT DOCUMENTS

| | | | | |
|---|---|---|---|---|
| 5,723,093 A | * | 3/1998 | De Bruyne et al. | 422/81 |
| 6,536,262 B2 | * | 3/2003 | Baldauf et al. | 73/61.47 |
| 7,135,870 B2 | * | 11/2006 | Mohajer et al. | 324/639 |
| 7,437,959 B1 | * | 10/2008 | Chadwick et al. | 73/864.56 |
| 7,921,739 B2 | * | 4/2011 | Fjerdingstad et al. | 73/863.71 |
| 2002/0121129 A1 | * | 9/2002 | Baldauf et al. | 73/61.47 |
| 2005/0264302 A1 | * | 12/2005 | Mohajer et al. | 324/639 |
| 2010/0199939 A1 | * | 8/2010 | Cottell | 123/1 A |
| 2013/0098844 A1 | * | 4/2013 | Forstmeier et al. | 210/739 |

FOREIGN PATENT DOCUMENTS

| | | | |
|---|---|---|---|
| GB | 2164021 | * | 3/1986 |
| GB | 2357710 | * | 1/2001 |

* cited by examiner

*Primary Examiner* — Hezron E Williams
*Assistant Examiner* — Hoang Nguyen
(74) *Attorney, Agent, or Firm* — Elizabeth R. Hall

(57) ABSTRACT

A method and device for generating an ongoing consistent velocity within a pipeline flow in order to achieve fluid homogeneity prior to oil water measurement. A recirculation flow loop withdraws flow from a first point in a pipeline, accelerates that flow with a pump, and reinjects the outflow from the pump through turbulence inducing outlets at a second point in the pipeline upstream of the first flow withdrawal point. The increased turbulence and mixing of the fluid flowing in the pipeline enhances the homogeneity of the oil/water suspension. The more homogeneous fluid recirculating in the flow loop passes through a measurement probe of an oil/water detector, thus increasing the accuracy of the oil/water measurement of the fluid.

19 Claims, 4 Drawing Sheets

US 9,134,204 B2

APPARATUS AND METHOD FOR MAINTAINING CONSISTENT FLUID VELOCITY AND HOMOGENEITY IN A PIPELINE

CROSS REFERENCE TO RELATED APPLICATIONS

This application claims priority to U.S. Provisional Patent Application Ser. No. 61/574,712, filed Aug. 8, 2011 by inventor Kam Mohajer and entitled "Apparatus and Method for Maintaining Consistent Velocity and Homogeneity in a Pipeline."

BACKGROUND OF THE INVENTION

1. Field of the Invention

The present invention relates in general to a device and method for increasing the accuracy of oil and water measurement in fluid flowing through a pipeline. More particularly, the present invention relates to a device and method for generating a consistent fluid velocity and homogeneity in a pipeline prior to the measurement of oil and water in the fluid.

2. Description of the Related Art

The accurate measurement of the water to oil ratio in the oil produced from a well is an important aspect of optimizing oil production from that well. Yet the measurement of water content in produced oil relies on accurate water to oil measurements being made on a homogenous fluid.

To date, achieving the high flow velocities necessary to achieve homogeneity of a highly viscous oil/water mixture flowing through a pipeline has been very difficult, or even impossible, to achieve.

There is a critical need for a simple, reliable, and quick method of maintaining high flow velocity and fluid homogeneity in produced oil flowing through a pipeline.

SUMMARY OF THE INVENTION

A method and device for generating an ongoing consistent velocity within a pipeline flow in order to achieve fluid homogeneity prior to oil water measurement. A recirculation flow loop withdraws flow from a first point in a pipeline, accelerates that flow with a pump, and reinjects the outflow from the pump through turbulence inducing outlets at a second point in the pipeline upstream of the first flow withdrawal point. The increased turbulence and mixing of the fluid flowing in the pipeline enhances the homogeneity of the oil/water suspension. The more homogeneous fluid recirculating in the flow loop passes through a measurement probe of an oil/water detector, thus increasing the accuracy of the oil/water measurement of the fluid.

One embodiment of the present invention includes a recirculating flow loop comprising: (a) a tubular fluid intake nozzle having a first intake nozzle end extending radially inwardly through a first side of a pipeline having a petroleum fluid flowing through the pipeline from an upstream end of the pipeline to a downstream end of the pipeline and a second intake nozzle end external to the pipeline, wherein the first intake nozzle end is sealingly closed and wherein the intake nozzle has an inlet opening penetrating a wall of the intake nozzle positioned within an interior of the pipeline with the inlet opening facing the upstream end of the pipeline; (b) an intake piping having a first leg attached to the second intake nozzle end and a second leg joined at an angle to the first leg where the second leg runs approximately parallel the pipeline; (c) a pump having an inlet and an outlet, wherein the inlet is attached to the second leg of the intake piping; (d) an injection pipe attached to the outlet of the pump at a first end of the injection pipe, the injection pipe including a detector module mounted adjacent the pump outlet, wherein the detector module has a measurement probe radially extending through a centerline of the injection pipe; and (e) a tubular injection nozzle having a first injection nozzle end attached to a second end of the injection pipe and a second injection nozzle end extending radially inwardly through the first side of the pipeline upstream of the fluid intake nozzle, wherein the second injection nozzle end is sealingly closed and wherein the injection nozzle has two diametrically opposed injection outlets penetrating a wall of the injection nozzle, wherein the two injection outlets are positioned within the interior of the pipeline and oriented transverse to a flow axis of the pipeline.

A second embodiment of the present invention includes a A recirculating flow loop comprising: (a) a pipeline having a multiphase fluid containing oil and water flowing through the pipeline from an upstream end of the pipeline to a downstream end of the pipeline along a flow axis; (b) a tubular fluid intake nozzle having a first intake end extending radially inwardly through a first side of the pipeline and a second intake end external to the pipeline, wherein the first intake nozzle end is sealingly closed and wherein the fluid intake nozzle has a circular inlet opening with a diameter equal to or less than the diameter of the fluid intake nozzle penetrating a wall of the intake nozzle, wherein the inlet opening is positioned approximately midway along a diameter of the pipeline facing the upstream end of the pipeline concentrically with the flow axis of the pipeline; (b) an intake piping having a first leg attached to the second intake end and a second leg joined at an angle to the first leg where the second leg runs approximately parallel the pipeline; (c) a pump having an inlet attached to the second leg of the intake piping and an outlet, wherein a diameter of the inlet is equal to the diameter of the intake piping and greater than a diameter of the outlet; (d) an injection pipe attached to the outlet of the pump with a diameter equal to the diameter of the pump outlet, the injection pipe having a detector module mounting a measurement probe radially extending through a centerline of the injection pipe, the detector module having an upstream end mounted on the pump outlet; and (e) a tubular injection nozzle having a first injection nozzle end mounted on a downstream end of the injection pipe and a second injection nozzle end extending radially inwardly through the first side of the pipeline upstream of the fluid intake nozzle, wherein the second injection nozzle end is sealingly closed and wherein the injection nozzle has two diametrically opposed injection outlets penetrating a wall of the injection nozzle, wherein the two injection outlets are positioned within the interior of the pipeline a distance of about 10% of a length of the diameter of the pipeline from the first side of the pipeline and oriented transverse to the flow axis of the pipeline.

A third embodiment of the present invention includes a method for measuring a water concentration of fluid flowing through a pipeline, the method comprising the steps: (a) installing a recirculating flow loop on the pipeline having an axis of fluid flow through the pipeline from an upstream end of the pipeline to a downstream end of the pipeline, the flow loop positioned external to the pipeline with a fluid intake nozzle penetrating the pipeline at a first point and an injection nozzle penetrating the pipeline at a second point upstream of the first point, wherein the flow loop further comprises an intake piping, a pump, and an injection pipe having a measurement probe radially extending into a center of the injection pipe; (b) removing a sample of a petroleum fluid flowing downstream through the pipeline through the intake nozzle; (c) sending the fluid sample through the intake piping at a first velocity to the pump; (c) pumping the fluid sample from the intake piping into the injection pipe at a second velocity, wherein the second velocity is greater than the first velocity; (d) passing the fluid sample through the measurement probe; (e) measuring the water concentration of the fluid sample passing through the measurement probe; and (f) injecting the fluid sample that has passed through the measurement probe into the fluid flowing through the pipeline, wherein the injected fluid sample enters the fluid flow at the second velocity upstream of the intake nozzle transverse to the flow axis of the fluid.

A fourth embodiment of the present invention includes a method for measuring the water concentration in a multi-phase fluid flowing through a pipeline, the method comprising the steps: (a) installing a recirculating flow loop on the pipeline, the flow loop comprising (i) a tubular fluid intake nozzle having a first intake nozzle end extending radially inwardly through a first side of the pipeline having a petroleum fluid flowing through the pipeline from an upstream end of the pipeline to a downstream end of the pipeline and a second intake nozzle end external to the pipeline, wherein the first intake nozzle end is sealingly closed and wherein the intake nozzle has an inlet opening penetrating a wall of the intake nozzle positioned within an interior of the pipeline with the inlet opening facing the upstream end of the pipeline; (ii) an intake piping having a first leg attached to the second intake nozzle end and a second leg joined at an angle to the first leg where the second leg runs approximately parallel the pipeline; (iii) a pump having an inlet and an outlet, wherein the inlet is attached to the second leg of the intake piping; (iv) an injection pipe attached to the outlet of the pump at a first end of the injection pipe, the injection pipe including a detector module mounted adjacent the pump outlet, wherein the detector module has a measurement probe radially extending through a centerline of the injection pipe; and (v) a tubular injection nozzle having a first injection nozzle end attached to a second end of the injection pipe and a second injection nozzle end extending radially inwardly through the first side of the pipeline upstream of the fluid intake nozzle, wherein the second injection nozzle end is sealingly closed and wherein the injection nozzle has two diametrically opposed injection outlets penetrating a wall of the injection nozzle, wherein the two injection outlets are positioned within the interior of the pipeline and oriented transverse to a flow axis of the pipeline; (b) removing a sample of the petroleum fluid through the inlet opening of the intake nozzle; (c) sending the fluid sample through the intake piping at a first velocity to the inlet of the pump; (c) pumping the fluid sample into the injection pipe at a second velocity, wherein the second velocity is greater than the first velocity; (d) passing the fluid sample through the measurement probe; (e) measuring the water concentration of the fluid sample passing through the measurement probe; (f) injecting the fluid sample that has passed through the measurement probe into the fluid flowing through the pipeline, wherein the injected fluid sample enters the fluid flow transverse to the flow axis of the fluid as the injected fluid sample exits two injection outlets to create two counter rotating vortices in the fluid flowing past the injection nozzle.

The foregoing has outlined rather broadly several aspects of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed might be readily utilized as a basis for modifying or redesigning the structures for carrying out the same purposes as the invention. It should be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

Figure 1:
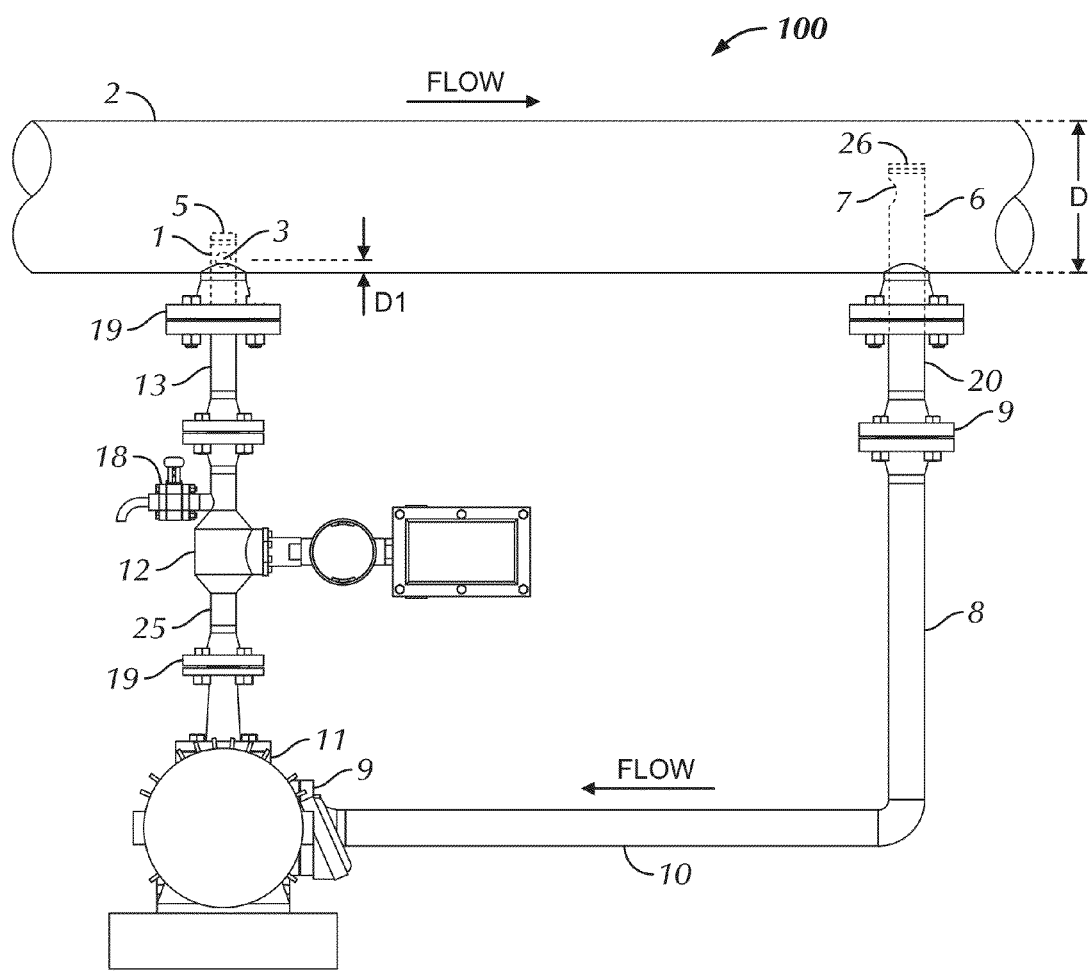
FIG. 1 is a side view of the oil/water ratio measurement system of the present invention installed in a horizontal pipeline carrying a two phase oil and water mixture.

It is noted that like reference characters designate like or similar parts throughout the drawings. The figures, or drawings, are not intended to be to scale. For example, purely for the sake of greater clarity in the drawings, wall thicknesses and spacings are not dimensioned as they actually exist in the assembled embodiments.

DESCRIPTION OF THE PREFERRED
EMBODIMENTS OF THE APPARATUS

Embodiments of the present invention relate to a method and apparatus for generating a consistent fluid velocity and homogeneity in a pipeline prior to the measurement of the ratio of oil and water in the fluid. More particularly, the present invention relates to the insertion of a measurement loop in a pipeline that includes a suction nozzle to extract a representative fluid sample from the main pipeline for oil/water measurement, pump for increasing the fluid flow in the measurement loop, and an injection nozzle designed to inject the extracted high velocity fluid sample back into the fluid flow in the main pipeline with sufficient turbulent mixing upstream of an oil/water ratio measurement instrument.

Referring to FIG. 1, a recirculating flow loop 100 of the present invention is shown installed on a horizontal section of a pipeline carrying a two phase oil water mixture. Such two phase mixtures are typical of the fluids produced from oil wells. The diameter of the pipeline is typically sized for the expected initial production rate for the well or wells which it services. With declining flows, lower velocities of the produced fluids aggravate a tendency for gravity induced vertical gradients in the oil/water ratios in the fluid passing through flowlines.

The more dense water phase tends to migrate towards the bottom side of a horizontal line, while the less dense oil phase tend to migrate towards the upper side of a horizontal line. The present invention provides sufficient turbulent mixing upstream of a conventional oil/water ratio measurement instrument to ensure that a substantially uniform, unstratified fluid mixture is sensed by the instrument.

As seen in FIG. 1, the recirculating flow loop 100 is attached to a horizontal main pipeline 2. The recirculating flow loop 100 has a fluid intake 6, a turbulence inducing injection nozzle 1 with an injection outlet 3, an oil-water ratio detector instrument module 12, a sampling valve 18, and a motorized pump 11.

The flow loop 100 flow path is constructed of straight pipe segments, flanges, elbows, a tee connection, a sampling valve, and optional ball valves for system isolation. The flow loop 100 is generally U-shaped with the legs of the U perpendicular to the axis of the main horizontal pipeline 2 and a horizontal central section connecting to the two legs of the U at their lower ends.

In FIG. 1, the flow direction shown in the main pipeline 2 is from left to right. The fluid intake nozzle 6 for the flow loop 100 is a short tubular section which extends radially inwardly into the main pipeline 2 and projects outwardly beyond the wall of main pipeline 2 a short distance. The fluid intake nozzle 6 is sealingly welded into the wall of the main pipeline 2 at its penetration.

The fluid intake nozzle 6 has a first end that extends radially inwardly to the centerline or beyond of the pipeline 2. On its transverse end interior to the pipeline 2, the fluid intake nozzle 6 has a flat plate end cap 26 welded closure transverse to the axis of the fluid intake. A circular inlet opening 7 facing upstream and located concentrically with the axis of the main pipeline 2 penetrates the wall of the fluid intake nozzle 6 to admit fluid. The diameter of the circular inlet opening 7 is typically equal to or slightly less than the diameter of the pipe of the fluid intake 6.

The end of the fluid intake 6, located externally to the pipeline 2, is transversely mounted on an intake flange 9 which is sealingly connected either to an optional full opening ball valve (not shown) or another similar of a pup joint 20 in order to connect to the rest of the recirculating flow loop 100. Ball valves may be utilized on both the inlet and outlet ends of the recirculating flow loop 100 in the event that it is desired to isolate the recirculating flow loop 100 from the main pipeline 2 in order to permit equipment servicing without shutting down pipeline operation. As shown in FIG. 1, the pup joint 20 is a short length of pipe having transverse large flanges 9 at both ends.

A first leg 8 of an intake pipe has a transverse intake flange 9 at its upper end and an elbow joint at its second lower end. The elbow joint joins the first leg 8 to a horizontal second leg 10. The horizontal second leg 10 typically has a transverse large intake flange 9 at its outlet (left) end. The diameters of the fluid intake pipes (i.e., the pup joint 20, the intake pipe 8 and the second leg 10) are all the same. In the event that a ball valve is substituted for the pup joint 20, the bore of the ball valve is selected to be substantially the same as for the bores of the pipes on the inlet side of the pump 11.

The pump 11 is provided with a drive motor to provide motive power for operation. The intake flange 9 on the pump 11 inlet has a diameter that is equal to or larger than the diameter flange 19 on the pump outlet. A preferred embodiment of the pump 11 will have a larger diameter intake flange 9 than the outlet flange 19. Likewise, although not required, the intake pipe will preferably have a larger diameter than the injection pipe connected to the pump outlet.

An important element of the flow loop 100 design is the selection of the pump size. The pump 11 is selected to provide a preferred constant fluid velocity of about 10-15 fps at the pump discharge.

Generally the fluid intake nozzle 6 of the flow loop 100 will remove approximately 20-30% of the pipeline flow in order to extract a representative flow from the main pipeline 2 for oil/water measurement. The pump 11 and the injector nozzle 1 are selected to increase the velocity of the main pipeline flow when injecting the 20-30% volume back into the pipeline. The selected pipe diameter of the flow loop 100 is based on the flow rate of the pump 11.

The oil-water detector instrument module 12 is located immediately downstream of the pump 11 in order that the flow turbulence induced by the pump 11 will further enhance the desired flow mixing and tendency for a substantially uniform, unstratified fluid mixture flowing through the flow loop 100 prior to measurement.

Figure 3:
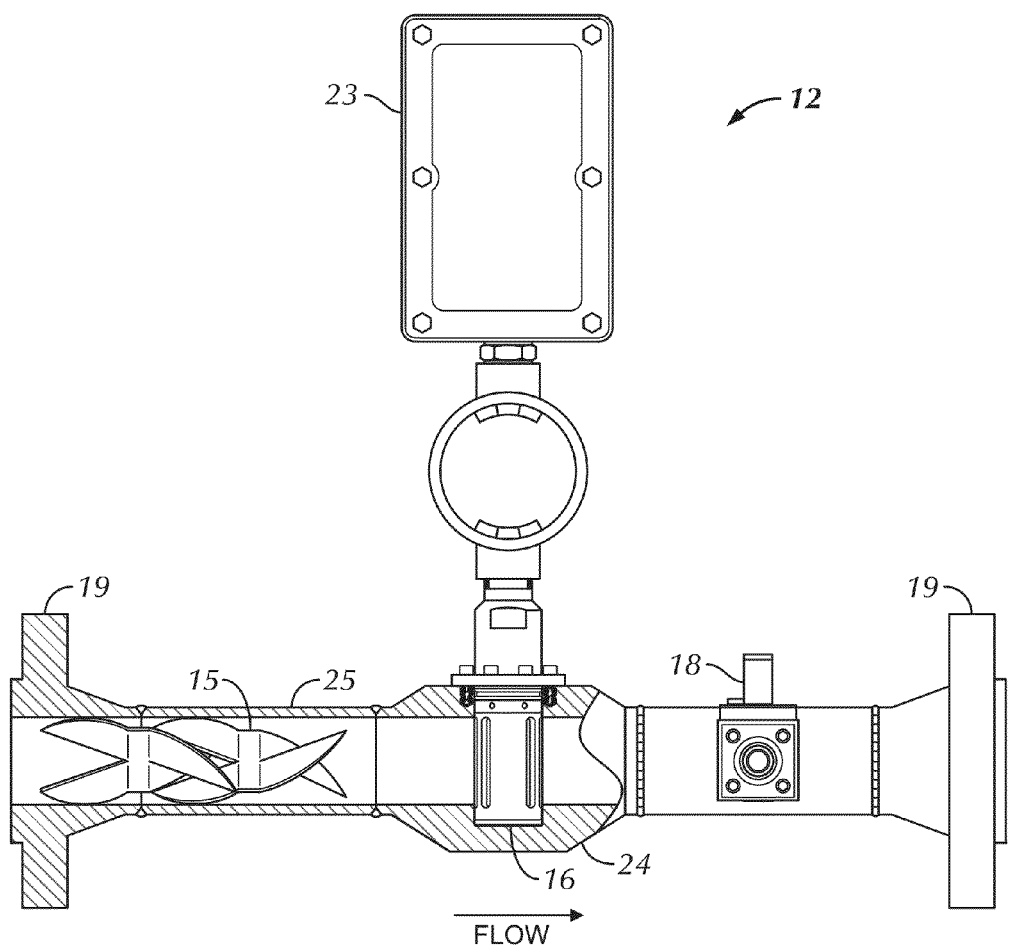
FIG. 3 is a partial longitudinal cross-sectional view of the oil/water ratio measurement sensor system, wherein an optional flow turbulator is installed immediately upstream of the sensors.

Referring to FIG. 3, the oil-water detector instrument module 12 sequentially from its entry end consists of an entry flange 19, a short pipe section 25 housing an optional static mixer 15, a cylindrical housing 24 providing a through flow path, a branch reducer tee mounting a laterally extending sampling valve 18 on its branch, and an exit flange 19 on the outlet end.

The cylindrical housing 24 has an intersecting central cylindrical cavity transverse to the flow path through the module wherein the sensors of the measurement probe 16 are positioned. The measurement probe 16 is attached by a centrally located sealing flange connection to the cylindrical housing 24. The measurement probe 16 has an attached measurement processor 23. The processor 23 has a measurement processor housing externally located. The processor 23 and its associated electronics process and transmit the data obtained by the measurement probe 16.

A pup joint 13 has a central pipe section with a coaxial flange 19 at each end. The pup joint 13 can be selectably replaced with a ball valve.

The injection nozzle 1 has a short tubular section which extends radially inwardly into the main pipeline 2 and projects outwardly beyond the wall of main pipeline 2 a short distance. The injection nozzle 1 is sealingly welded into the wall of the main pipeline 2 at its penetration.

The injection nozzle 1 reintroduces the homogenous fluid from the loop into the main pipeline. In doing so, it performs two key functions for creating a homogenous flow prior to the removal of fluid from the pipeline through the fluid intake nozzle 6. The first key function is the injection of the fluid from the flow loop 10 into the main pipeline flow, where the injected fluid has an increased velocity assured by the selection of a large pump 11. The second key function is derived from the design and placement of the injector nozzle itself.

The injection nozzle 1 extends radially inwardly past the wall of the main pipeline 2 by a distance approximately equal to its diameter. On its transverse end interior to the pipeline 2, the injection nozzle 1 has a welded transverse end cap 5 serving as a closure perpendicular to the axis of the injection nozzle.

A pair of diametrically opposed elliptical injection outlet openings 3 penetrates the wall of the injection nozzle 1 between the end cap 5 and the interior wall of the main pipeline 2. The injection outlet openings 3 are oriented transverse to the flow axis of the main pipeline 2, and their centers are located at a distance D1 from the interior wall of the main pipeline 2. D1 typically varies between about 5% to about 15% and is preferably approximately 10% of the diameter D of the main pipeline 2.

Figure 2:
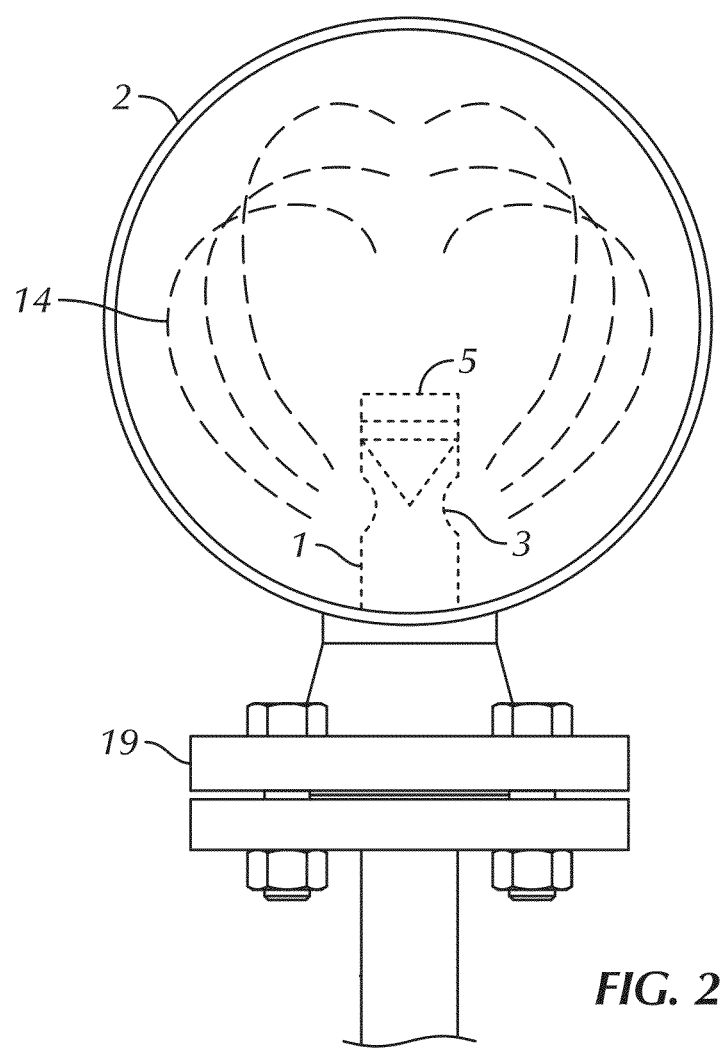
FIG. 2 is a transverse sectional view of the injection nozzle of the present invention installed in a two phase flowline, indicating the flow pattern emanating from the outlet openings of the nozzle.

The injection nozzle 1 injects the increased velocity flow from the loop 10 in two streams exiting from the openings 3. The exiting high velocity fluid is angled toward the side walls of the main pipeline 2. The injection nozzle 1 is placed such that the exiting fluid streams contact the main pipe 2 near the centers of the side walls. As shown in FIG. 2, these two streams create counter-rotating vortices 14 which when combined with the increase in velocity mix the main pipeline flow to homogeneity. In this way, a homogenous zone is created and maintained in the main pipeline between the injection nozzle 1 and fluid intake nozzle 6.

Figure 4:
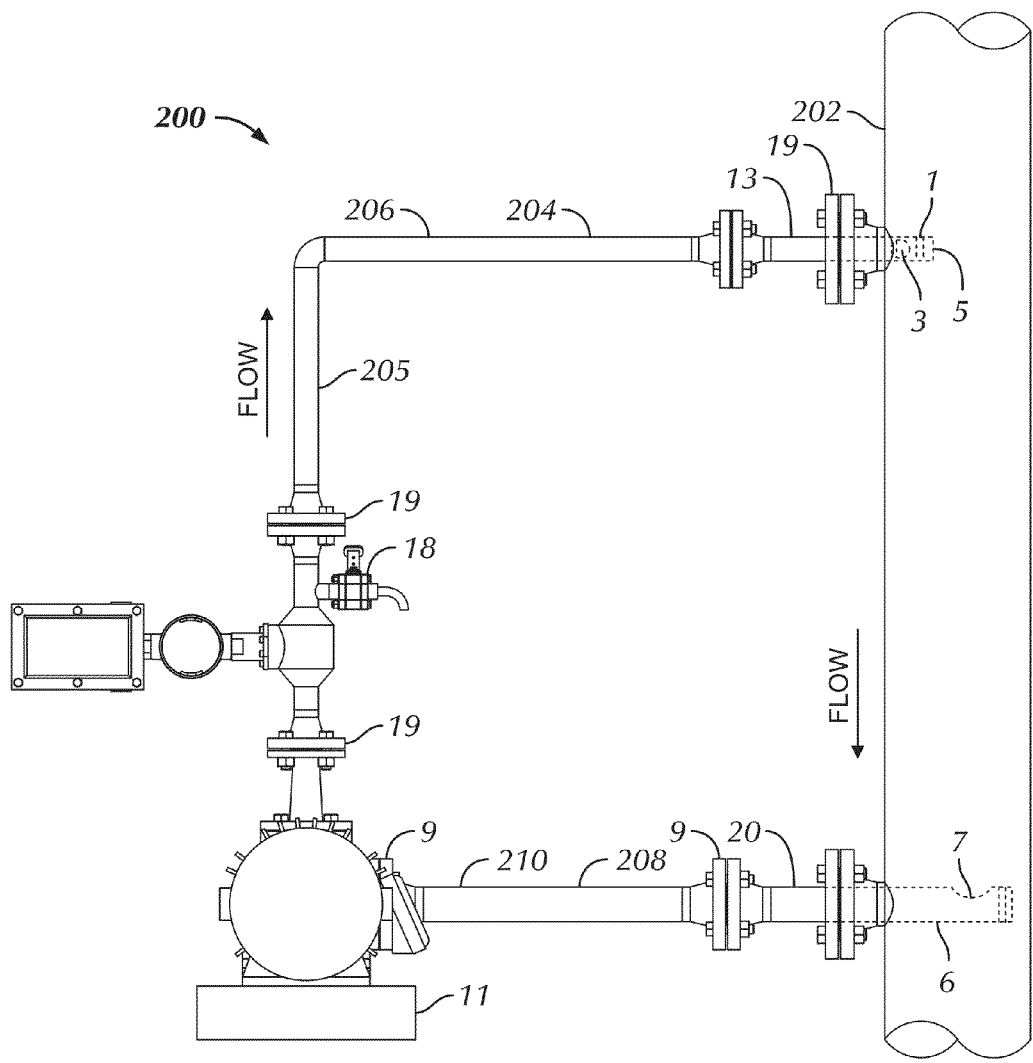
FIG. 4 corresponds to FIG. 1, but shows the configuration of the measurement system suitable for installation in a vertical pipeline section.

FIG. 4 illustrates a recirculating flow loop 200 installed on a vertical section of a pipeline 202 carrying a two phase oil water mixture. Only minor differences in the makeup of the recirculating systems exist between the recirculating flow loops for the horizontal pipeline 100 and the vertical pipeline 200. The operation of the two recirculating flow loops is substantially identical.

The recirculating flow loop 200 also contains a fluid intake nozzle 6, a turbulence inducing injection nozzle 1 with a pair of outlets 3, an oil-water ratio detector instrument module 12, a sampling valve 18, and a motorized pump 11 attached to a vertical main pipeline 202. As before, the recirculating flow loop 200 flow path is constructed of straight pipe segments, flanges, elbows, a tee connection, a sampling valve, and, optionally, ball valves for system isolation. The flow loop is generally U-shaped with the legs of the U horizontal and perpendicular to the axis of the main vertical pipeline 202 and a vertical central section connecting to the two legs of the U at their lower (left) ends.

FIG. 4 shows the flow loop 200 when the flow direction in the main pipeline 202 is downward. The fluid intake nozzle 6 for the flow loop 200 is substantially the same as described for the flow loop 100. The fluid intake nozzle 6 is a short tubular section which extends radially inwardly into the main pipeline 202 and projects outwardly beyond the wall of main pipeline 202 a short distance. The fluid intake nozzle 6 is sealingly welded into the wall of the main pipeline 202 at its penetration.

On its external end, the fluid intake nozzle 6 has a transversely mounted intake flange 9 which can be sealingly connected either to an optional fully opening ball valve (not shown) or another similar intake flange 9 of a pup joint 20 in order to connect to the rest of the recirculating flow loop 200. Ball valves may be utilized on both the inlet and outlet ends of the recirculating flow loop 200 in the event that it is desired to isolate the recirculating flow loop 200 from the main pipeline 202 in order to permit equipment servicing without shutting down pipeline operation. As shown in FIG. 4, the pup joint 20 is a short length of pipe having transverse intake flanges 9 at both ends.

For the vertical pipeline 202, the intake piping 208 has a horizontal leg 210 having a transverse intake flange 9 at both ends. The diameters of the pipes for the fluid intake nozzle 6, the pup joint 20, and the intake piping 208 are all the same. In the event that a ball valve is substituted for the pup joint 20, the bore of the ball valve is selected to be substantially the same as for the bores of the pipes on the inlet side of the pump 11.

The pump 11 is provided with a drive motor to provide motive power for operation. The pump 11 typically has a larger diameter intake flange 9 on its inlet and a smaller diameter exit flange 19 on its outlet.

The vertically oriented oil-water detector instrument module 12 is located immediately downstream of the pump 11 in order that the flow turbulence induced by the pump 11 will further enhance the desired flow mixing leading to a substantially uniform distribution of the entrained oil droplets in the water of the flow loop 200 prior to measurement.

Referring to FIG. 3, the oil-water detector instrument module 12 sequentially from its entry end consists of an exit flange 19, a short pipe section 25 housing an optional static mixer 15, a housing 24 providing a through flow path, a branch reducer tee mounting a laterally extending sampling valve 18 on its branch, and an exit flange 19 on the outlet end.

The cylindrical housing 24 has an intersecting central cylindrical cavity transverse to the flow path through the module wherein the sensors of the measurement probe 16 are positioned. The measurement probe 16 is attached by a centrally located sealing flange connection to the cylindrical housing 24. The measurement probe 16 has an attached externally located measurement processor 12 with its associated electronics. The measurement processor and its electronics process and transmit the data obtained by the sensors of the measurement probe 16.

The outlet piping 204 from the outlet end of the vertically oriented oil-water detector instrument module 12 consists sequentially of an exit flange 19, vertical leg 205, a pipe elbow, a horizontal leg 206, and a second exit flange 19. Connected to the outlet end of outlet piping 204 is a pup joint 13 which has a short central pipe section with a coaxial exit flange 19 at each end. The pup joint 13 can be selectably replaced with a ball valve.

The injection nozzle 1, like that described for the horizontal flow loop 100, consists of a short tubular section which extends radially inwardly into the main pipeline 202 and projects outwardly beyond the wall of main pipeline 202 a short distance. The injection nozzle 1 is sealingly welded into the wall of the main pipeline 202 at its penetration.

The injection nozzle 1 extends radially inwardly past the wall of the main pipeline 202 by a distance approximately equal to its diameter. On its transverse end interior to the pipeline 202, the injection nozzle 1 has a flat plate welded transverse end cap 5 serving as a closure perpendicular to the axis of the injection nozzle. A pair of diametrically opposed elliptical outlet openings 3 penetrates the wall of the injection nozzle 1 between the end cap 5 and the interior wall of the main pipeline 202. The outlet openings are oriented transverse to the flow axis of the main pipeline 202, with their centers approximately 5% to 15% (preferably about 10%) of the diameter of the main pipeline 202 away from the interior wall of the main pipeline 202.

Operation of the Recircuting Flow Loop

The recirculating flow loops 100 and 200 increase the accuracy of oil/water detection in petroleum products flowing through a pipeline. Recirculating flow loops 100 and 200 operate in a similar manner as described below for the flow loop 100.

Recirculating flow loops with their attached oil/water detection modules 12 should be utilized in any application requiring accurate oil/water measurement but suffering from low or inconsistent velocities. Operators may choose to install loops on individual well heads, or after manifolds integrating several well heads. In the later case in particular, varying velocities from different wells can make consistent oil/water measurements difficult without the use of a recirculating flow loop.

The recirculation flow loop 100 withdraws fluid flowing past a first point in a pipeline, accelerates the extracted fluid flow with a pump 11, and reinjects the outflow from the pump through turbulence inducing outlets 3 at a second point in the pipeline upstream of the first flow withdrawal point. The increased turbulence and mixing of the fluid flowing in the pipeline decreases the size of the oil/water droplets suspended in the fluid and enhances the homogeneity of the suspension. The more homogeneous fluid recirculating in the flow loop passes through a measurement probe 16 of an oil/water detector 12, thus increasing the accuracy of the oil/water measurement of the fluid.

The operation of the recirculating flow loop 100 depends upon using additional energy imparted to an incoming pipeline flow stream consisting of oil droplets dispersed in water, wherein the energy serves to substantially uniformize the distribution of the oil droplets. The additional energy is imparted by a pump, and the accelerated flow stream of the pump is diffused in vortex turbulence imparted to the incoming, typically nonuniform pipeline flow stream. With sufficient turbulent mixing of the combined flow stream as a result of the induced turbulence, a substantially uniform oil/water distribution is produced. An additional benefit of using the injected pump flow stream is the local acceleration of the pipeline flow, which also contributes to the induced turbulent mixing.

Because the injected pump flow stream is injected transverse to the pipeline axis and adjacent to the transversely curved interior wall of the pipeline, turbulent vortices 14 result, as seen in FIG. 2. Within a certain number of pipe diameters of flow travel beyond the injection point, these vortices 14 generate mixing by flowing across the entire cross section of the pipeline.

The flow supply for the pump 11 is drawn from the center of the pipeline a sufficient distance downstream from where the injected high velocity pump flow stream enters the pipeline such that a substantially uniform flow stream due to good upstream mixing from the induced turbulence has occurred. Oil/water concentrations are instrumentally measured between the pump 11 and the point where the pump flow is injected into the pipeline at the injection nozzle 1. The turbulence in the recirculating flow loop immediately downstream of the pump outlet further enhances the uniformization of the oil/water distribution in the flow stream.

Advantages of the Recirculating Flow Loop

The incorporation of a recirculating flow loop offers several key advantages to end users seeking accurate oil water measurement in addition to a homogenous flow. The consistency of the measurement environment created by the recirculating flow loop eliminates variances in flow conditions that affect accurate oil/water measurement. One such variance is the change in oil/water droplet ratios in the water continuous phase. While a disparity in droplet size will continue to exist in the homogenous flow within the loop, a constant fluid flow velocity ensures the consistency of the ratio of oil and water within the droplets.

Another major advantage of the recirculating flow loop described herein is that in heavy oil conditions, highly viscous fluids can accumulate on the sensor probes of oil/water measurement devices thereby affecting the accuracy of the oil/water measurement and requiring regular maintenance and cleaning of the measurement probes. Using the described recirculating flow loop a high fluid velocity is maintained across the sensor probe surface and inhibits the accumulation of fluids on the probe surface.

One additional advantage of a measurement loop is the handling of water slugs or brief peaks of high water in the pipeline. Currently available oil/water measurement devices installed to measure the oil/water ratio in pipeline flow, do not accurately represent these peaks of high water slugs because of the minimal exposure of the water slugs to the oil/water measurement device. In contrast, the described recirculating flow loop disperses the water slugs in such a way that the amplitude of the water peaks is reduced and the time of exposure to the measurement device is increased generating a smaller signal over a greater period of time to yield a more accurate measurement of the oil/water ratio.

The described recirculating flow loops can also incorporate multiple measurement devices such as automatic samplers, densitometers, etc. into a single recirculating loop, thus limiting the need for multiple device installations and ensuring that all devices access the same homogenous flow.

The installation of a measurement loop for the purposes or oil/water measurement allows measurement devices to operate in optimized conditions. The device can be easily installed and eliminates maintenance issues often associated with heavy oils and/or low velocities. Using a pump to generate a constant velocity well above API standards, a measurement loop creates a homogenous flow for accurate oil/water measurement. In addition, it eliminates the effects of varying droplet sizes by turning them into measurable constant, and water slugs are dispersed within the flow for more accurate measurement. In short, a measurement loop generates a homogenous flow while also eliminating or removing the effects of many of the varying field conditions which often plague oil/water measurement in general and heavy oil production in particular.

Efficient petroleum production processing obtainable using the more accurate oil/water measurement data from the recirculating flow loop described above has significant economic advantages over less carefully controlled processing.

The foregoing has outlined the basic features of the recirculating flow loop. However, it should be appreciated by those skilled in the art that the conception and the specific embodiments disclosed might be readily utilized as a basis for modifying or redesigning the system or the method described for carrying out the purpose of the invention as described. It should be realized by those skilled in the art that such equivalent constructions do not depart from the spirit and scope of the invention as set forth in the appended claims.

What is claimed is:

1. A recirculating flow loop comprising:
   (a) a tubular fluid intake nozzle having a first intake nozzle end extending radially inwardly through a first side of a pipeline having a petroleum fluid flowing through the pipeline from an upstream end of the pipeline to a downstream end of the pipeline and a second intake nozzle end external to the pipeline, wherein the first intake nozzle end is sealingly closed, wherein the intake nozzle has an inlet opening facing upstream and located concentrically with a flow axis of the pipeline, wherein the inlet opening penetrates a wall of the intake nozzle positioned within an interior of the pipeline, and wherein the fluid intake nozzle removes approximately 20-30% of the fluid flowing through the pipeline to extract a representative sample of the fluid flow;
   (b) an intake piping having a first leg attached to the second intake nozzle end and a second leg joined at an angle to the first leg where the second leg runs approximately parallel the pipeline;
   (c) a pump having an inlet and an outlet, wherein the inlet is attached to the second leg of the intake piping;
   (d) an injection pipe attached to the outlet of the pump at a first end of the injection pipe, the injection pipe including a detector module mounted adjacent the pump outlet, wherein the detector module has a measurement probe radially extending through a centerline of the injection pipe; and
   (e) a tubular injection nozzle having a first injection nozzle end attached to a second end of the injection pipe and a second injection nozzle end extending radially inwardly through the first side of the pipeline upstream of the fluid intake nozzle, wherein the second injection nozzle end is sealingly closed, wherein the injection nozzle has two diametrically opposed injection outlets penetrating a wall of the injection nozzle, wherein the two injection outlets are positioned within the interior of the pipeline and oriented transverse to a flow axis of the pipeline, wherein the two injection outlets are further oriented perpendicular to the inlet opening, and wherein the two injection outlets are configured such that the fluid exiting from them contacts the pipeline substantially near the center of opposing side walls of the pipeline.

2. The recirculating flow loop of claim 1, wherein a diameter of the inlet opening is equal to or less than a diameter of the fluid intake nozzle.

3. The recirculating flow loop of claim 1, wherein the intake piping has a larger diameter than the injection pipe.

4. The recirculating flow loop of claim 1, wherein the detector module includes a static mixer between the outlet end of the pump and the measurement probe.

5. The recirculating flow loop of claim 1, wherein the measurement probe is in communication with a measurement processor.

6. The recirculating flow loop of claim 1, wherein the injection nozzle extends radially inward of the first side of the pipeline by a distance about equal to a diameter of the injection nozzle.

7. The recirculating flow loop of claim 1, wherein the injection outlets are located from the first side of the pipeline a distance equal to about 5% to about 15% of a diameter of the pipeline.

8. The recirculating flow loop of claim 1, wherein the injection outlets are located from the first side of the pipeline a distance equal to about 10% of a diameter of the pipeline.

9. A recirculating flow loop comprising:
    (a) a pipeline having a multiphase fluid containing oil and water flowing through the pipeline from an upstream end of the pipeline to a downstream end of the pipeline along a flow axis;
    (b) a tubular fluid intake nozzle having a first intake end extending radially inwardly through a first side of the pipeline and a second intake end external to the pipeline, wherein the first intake nozzle end is sealingly closed with a flat plate end, wherein the fluid intake nozzle has a circular inlet opening with a diameter equal to or less than the diameter of the fluid intake nozzle penetrating a wall of the intake nozzle, wherein the inlet opening is positioned approximately midway along a diameter of the pipeline facing the upstream end of the pipeline concentrically with the flow axis of the pipeline, and wherein the fluid intake nozzle removes approximately 20-30% of the fluid flowing through the pipeline to extract a representative sample of the fluid flow;
    (c) an intake piping having a first leg attached to the second intake end and a second leg joined at an angle to the first leg where the second leg runs approximately parallel the pipeline;
    (d) a pump having an inlet attached to the second leg of the intake piping and an outlet, wherein a diameter of the inlet is equal to the diameter of the intake piping and greater than a diameter of the outlet;
    (e) an injection pipe attached to the outlet of the pump with a diameter equal to the diameter of the pump outlet, the injection pipe having a detector module mounting a measurement probe radially extending through a centerline of the injection pipe, the detector module having an upstream end mounted on the pump outlet; and
    (f) a tubular injection nozzle having a first injection nozzle end mounted on a downstream end of the injection pipe and a second injection nozzle end extending radially inwardly through the first side of the pipeline upstream of the fluid intake nozzle, wherein the second injection nozzle end is sealingly closed and wherein the injection nozzle has two diametrically opposed injection outlets penetrating a wall of the injection nozzle, wherein the two injection outlets are positioned within the interior of the pipeline a distance of about 10% of a length of the diameter of the pipeline from the first side of the pipeline and oriented transverse to the flow axis of the pipeline, wherein the two injection outlets are further oriented perpendicular to the inlet opening, and wherein the injection outlets are configured such that the fluid exiting from them contacts the pipeline substantially near the center of opposing side walls of the pipeline.

10. The recirculating flow loop of claim 9, wherein the detector module includes a static mixer between the outlet end of the pump and the measurement probe.

11. The recirculating flow loop of claim 9, wherein the measurement probe is in communication with a measurement processor.

12. The recirculating flow loop of claim 9, wherein the injection nozzle extends radially inward of the first side of the pipeline by a distance about equal to a diameter of the injection nozzle.

13. A method for measuring a water concentration of fluid flowing through a pipeline, the method comprising the steps:
    (a) installing the recirculating flow loop according to claim 9 on the pipeline having an axis of fluid flow through the pipeline from an upstream end of the pipeline to a downstream end of the pipeline, the flow loop positioned external to the pipeline with the fluid intake nozzle penetrating the pipeline at a first point and the injection nozzle penetrating the pipeline at a second point upstream of the first point;
    (b) removing a sample comprising about 20-30% of a petroleum fluid flowing downstream through the pipeline through the intake nozzle;
    (c) sending the fluid sample through the intake piping at a first velocity to the pump;
    (d) pumping the fluid sample from the intake piping into the injection pipe at a second velocity, wherein the second velocity is greater than the first velocity;
    (e) passing the fluid sample through the measurement probe;
    (f) measuring the water concentration of the fluid sample passing through the measurement probe; and
    (g) injecting the fluid sample that has passed through the measurement probe into the fluid flowing through the pipeline, wherein the injected fluid sample enters the fluid flow at the second velocity upstream of the intake nozzle transverse to the flow axis of the fluid.

14. The method of claim 13, further comprising pumping the fluid sample at the second velocity through a static mixer prior to passing the fluid sample through the measurement probe.

15. The method of claim 13, wherein from about 20% to about 30% of the fluid flowing through the pipeline is removed through the inlet opening to pass through the flow loop.

16. The method of claim 13, wherein the fluid sample is injected into the fluid flow through the pair of opposed injection outlets oriented towards two sides of the pipeline.

17. The method of claim 16, wherein the injection outlets are elliptical and are positioned within the lumen of the pipeline about a distance of about 10% of a diameter of the pipeline from a side of the pipeline penetrated by the injection nozzle.

18. The method of claim 13, wherein the injected fluid sample creates two counter rotating vortices in the fluid flowing through the pipeline thereby mixing the fluid flowing past the injection nozzle.

19. A method for measuring the water concentration in a multi-phase fluid flowing through a pipeline, the method comprising the steps:
- (a) installing a recirculating flow loop on the pipeline, the flow loop comprising
  - (i) a tubular fluid intake nozzle having a first intake nozzle end extending radially inwardly through a first side of the pipeline having a petroleum fluid flowing through the pipeline from an upstream end of the pipeline to a downstream end of the pipeline and a second intake nozzle end external to the pipeline, wherein the first intake nozzle end is sealingly closed with a flat plate end, wherein the fluid intake nozzle has a circular inlet opening with a diameter equal to or less than the diameter of the fluid intake nozzle penetrating a wall of the intake nozzle, wherein the inlet opening is positioned approximately midway along a diameter of the pipeline facing the upstream end of the pipeline concentrically with the flow axis of the pipeline;
  - (ii) an intake piping having a first leg attached to the second intake nozzle end and a second leg joined at an angle to the first leg where the second leg runs approximately parallel the pipeline;
  - (iii) a pump having an inlet and an outlet, wherein the inlet is attached to the second leg of the intake piping;
  - (iv) an injection pipe attached to the outlet of the pump at a first end of the injection pipe, the injection pipe including a detector module mounted adjacent the pump outlet, wherein the detector module has a measurement probe radially extending through a centerline of the injection pipe; and
  - (v) a tubular injection nozzle having a first injection nozzle end attached to a second end of the injection pipe and a second injection nozzle end extending radially inwardly through the first side of the pipeline upstream of the fluid intake nozzle, wherein the second injection nozzle end is sealingly closed, wherein the injection nozzle has two diametrically opposed injection outlets penetrating a wall of the injection nozzle, wherein the two injection outlets are positioned within the interior of the pipeline and oriented transverse to a flow axis of the pipeline, wherein the two injection outlets are further oriented perpendicular to the inlet opening, and wherein the injection outlets are configured such that the fluid exiting from them contacts the pipeline substantially near the center of opposing side walls of the pipeline;
- (b) removing a sample of the petroleum fluid through the inlet opening of the intake nozzle, wherein the sample represents approximately 20-30% of the fluid flowing through the pipeline;
- (c) sending the fluid sample through the intake piping at a first velocity to the inlet of the pump;
- (d) pumping the fluid sample into the injection pipe at a second velocity, wherein the second velocity is greater than the first velocity;
- (e) passing the fluid sample through the measurement probe;
- (f) measuring the water concentration of the fluid sample passing through the measurement probe; and
- (g) injecting the fluid sample that has passed through the measurement probe into the fluid flowing through the pipeline, wherein the injected fluid sample enters the fluid flow transverse to the flow axis of the fluid as the injected fluid sample exits two injection outlets to create two counter rotating vortices in the fluid flowing past the injection nozzle.

* * * * *